United States Patent
Mouchawar et al.

(10) Patent No.: US 6,731,980 B1
(45) Date of Patent: May 4, 2004

(54) SYSTEM AND METHOD FOR AUTOMATICALLY SETTING A PRE-VENTRICULAR ATRIAL BLANKING PERIOD

(75) Inventors: Nabil A. Mouchawar, Newhall, CA (US); Martin Cholette, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 363 days.

(21) Appl. No.: 10/011,930

(22) Filed: Oct. 29, 2001

(51) Int. Cl.[7] .............................................. A61N 1/362
(52) U.S. Cl. ............................................ 607/9; 607/17
(58) Field of Search .............................. 607/4, 9, 17, 25

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,729,376 A | 3/1988 | DeCote, Jr. | 128/419 PT |
| 4,788,980 A | 12/1988 | Mann et al. | 128/419 PG |
| 4,940,052 A | 7/1990 | Mann et al. | 128/419 PG |
| 4,969,467 A | 11/1990 | Callaghan et al. | 128/419 PG |
| 4,974,589 A * | 12/1990 | Sholder | 607/9 |
| 5,342,405 A | 8/1994 | Duncan | 607/17 |
| 5,350,410 A | 9/1994 | Kleks et al. | 607/28 |
| 5,466,254 A | 11/1995 | Helland | 607/123 |
| 5,573,550 A | 11/1996 | Zadeh et al. | 607/28 |
| 5,601,613 A | 2/1997 | Florio et al. | 607/14 |
| 5,620,471 A | 4/1997 | Duncan | 607/14 |
| 5,683,447 A | 11/1997 | Bush et al. | 607/126 |
| 5,685,315 A | 11/1997 | McClure et al. | 128/708 |
| 5,692,907 A | 12/1997 | Glassel et al. | 434/262 |
| 5,788,717 A | 8/1998 | Mann et al. | 607/14 |
| 5,991,656 A | 11/1999 | Olson et al. | 607/4 |
| 6,021,351 A | 2/2000 | Kadhiresan et al. | 607/19 |
| 6,029,087 A | 2/2000 | Wohlgemuth | 607/9 |
| 6,044,298 A | 3/2000 | Salo et al. | 607/17 |
| 6,052,620 A | 4/2000 | Gillberg et al. | 607/4 |

FOREIGN PATENT DOCUMENTS

EP 1123716 A2 * 8/2001 ............ A61N/1/39

* cited by examiner

*Primary Examiner*—Carl Layno

(57) ABSTRACT

An implantable cardiac stimulation system and associated method automatically adjust a pre-ventricular atrial blanking period such that far-field R-waves are not detected by the atrial channel as P-waves. The pre-ventricular atrial blanking period is dynamically adjusted to a period that causes the system to ignore an atrial sensed event that follows a prior atrial event without an intervening ventricular event.

32 Claims, 8 Drawing Sheets

SYSTEM AND METHOD FOR AUTOMATICALLY SETTING A PRE-VENTRICULAR ATRIAL BLANKING PERIOD

CROSS-REFERENCE TO RELATED APPLICATION

This application is related to copending U.S. patent application Ser. No. 09/662,440, now U.S Pat. No. 6,516,225, filed Sep. 15, 2000, titled "System And Method For Distinguishing Electrical Events Originating In The Atria From Far-Field Electrical Events Originating In The Ventricles As Detected By An Implantable Medical Device," which is incorporated herein by reference, and which is assigned to the same assignee as the present application.

FIELD OF THE INVENTION

This invention relates generally to an implantable cardiac stimulation device capable of sensing cardiac signals in at least one atrial chamber of the heart and one ventricular chamber of the heart. More specifically, the present invention is directed to a method for automatically determining a pre-ventricular atrial blanking period in order to prevent sensing of far-field R-waves in the atria.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. One or more heart chambers may be electrically stimulated depending on the location and severity of the conduction disorder.

A single-chamber pacemaker delivers pacing pulses to one chamber of the heart, either one atrium or one ventricle. Dual chamber pacemakers are now commonly available and can provide stimulation in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (a P-wave) is not detected by the atrial channel, a stimulating pulse will be delivered to depolarize the atrium and cause contraction. Following either a detected P-wave or an atrial pacing pulse, the ventricular channel attempts to detect a depolarization signal in the ventricle, known as an R-wave. If no R-wave is detected within a defined atrial-ventricular interval (AV interval, also referred to as AV delay), a stimulation pulse is delivered to the ventricle to cause ventricular contraction. In this way, rhythmic dual chamber pacing is achieved by coordinating the delivery of ventricular output in response to a sensed or paced atrial event.

One problem faced with the advent of dual-chambered pacemakers is that when a pacemaker delivers a stimulation pulse to the ventricle during an appropriate portion of a cardiac cycle, this pulse would be sensed on the atrial channel. Therefore, it has been a common practice to apply a post-ventricular atrial blanking (PVAB) period upon delivery of a ventricular stimulation pulse. This practice prevents saturation of the sense amplifiers of the atrial channel during the delivery of the ventricular pulse.

By disabling the atrial sense amplifier upon the delivery of a ventricular stimulating pulse, the atrial sense amplifier is not affected by the ventricular stimulation pulse. At a specified time interval after the delivery of a ventricular stimulating pulse, the atrial sense amplifiers are enabled again to sense intrinsic or evoked atrial events. The post ventricular atrial blanking period is typically on the order of 150 msec.

The post-ventricular atrial blanking period poses a new problem in that it may occur mid-way or even late in the atrial cycle, and may therefore result in the atrial channel not sensing the next intrinsic atrial event. Essentially, the atrial channel is "blinded" to rapid atrial rates, precluding proper diagnostic and therapeutic measures to be taken by the implanted cardiac device.

Instead, a missed atrial event would trigger an atrial stimulation pulse to be inappropriately delivered by the stimulation device. Such inappropriate pacing could endanger the patient by inducing a sequence of events that might induce cardiac arrhythmias. Therefore, the post-ventricular atrial blanking period is preferably kept as short as possible to allow sensing of high atrial rates, but long enough to prevent detection of the ventricular stimulation pulse or the subsequent afterpotential.

However, two other events may follow an intrinsic ventricular event that may also be sensed by the atrial channel: 1) a far-field R-wave due to the depolarization of the large ventricular mass creating a signal large enough to be detected in the atria, and 2) a retrograde conducted depolarization in patients with conduction pathways that allow the ventricular R-wave to be conducted back into the atria. Either of these events may be incorrectly detected by the atrial channel as an intrinsic P-wave, resulting in the false interpretation of the atrial rhythm.

Such atrial detection would trigger the delivery of another ventricular stimulation pulse at the end of a PV interval. This situation could lead to pacemaker-mediated tachycardia (PMT) since the ventricular stimulation rate is tracking a falsely interpreted atrial rate. To address this problem, the post-ventricular atrial blanking period is typically followed by a post-ventricular atrial refractory period (PVARP). The post-ventricular atrial refractory period is typically 100 to 150 msec long and allows detection of events, such as far-field R-waves or retrograde P-waves, but any events detected during this refractory period are not tracked for the purposes of delivering ventricular stimulation.

A far-field R-wave may also be detected by the atrial sensing circuits prior to the detection of an R-wave by the ventricular channel. In this situation, a post-ventricular atrial refractory period is not effective in preventing tracking of the inappropriately detected far-field R-wave by the atrial channel. Depending on electrode position, atrial sensitivity settings, and other factors, the likelihood of sensing far-field R-waves on the atrial channel will vary between patients. Because an intrinsic R-wave is not always sensed instantaneously, it is possible in some patients that a far-field R-wave is sensed on the atrial channel prior to the source R-wave being detected on the ventricular channel.

A far-field ventricular event inappropriately sensed by the atrial channel as a P-wave could cause a ventricular stimulation pulse to be delivered to the ventricle at a time when the ventricle has already depolarized. Stimulation of the ventricle during a time when the ventricle cannot depolarize will result in a loss of capture detection in devices equipped with automatic capture verification and thus invoke a high-energy back-up stimulation pulse and possibly a threshold test when these responses are not clinically indicated. In a worst-case scenario, stimulation of the ventricle during its repolarization phase can induce ventricular fibrillation, a potentially lethal result. Sensing a far-field ventricular signal by the atrial channel may also trigger automatic mode-switching due to the interpretation of a high atrial rate.

It would be desirable therefore to provide an automatically adjustable atrial blanking period in dual chamber or multi-chamber stimulation devices in order to ensure effective elimination of far-field R-wave sensing despite individual variations that affect the likelihood of far-field R-wave sensing.

SUMMARY OF THE INVENTION

The present invention addresses this need by providing an implantable cardiac stimulation device capable of dynamically adjusting a pre-ventricular atrial blanking period for the prevention of far-field R-wave sensing.

When operating according to an illustrative embodiment, the control system determines a minimum interval between an atrial event, either an atrial stimulation pulse or an intrinsic P-wave, and the subsequent intrinsic R-wave, known as the AR or PR interval, respectively. A minimum atrial refractory period is determined next by determining the shortest atrial refractory period setting that prevents two consecutive atrial events from being sensed with no intervening ventricular event. The maximum pre-ventricular atrial blanking period is then calculated as the difference between the minimum (PR or AR) interval and the minimum atrial refractory period.

Next, the pre-ventricular atrial blanking period is optimized to allow a maximum window of time for sensing atrial events by progressively shortening the pre-ventricular atrial blanking period from the calculated maximum until two consecutive atrial events occur, the second event presumably being a far-field R-wave. The pre-ventricular atrial blanking period is then set to a value equal to the setting at which far-field R-wave sensing first occurred plus a predefined safety margin.

The methods of the present invention thus provide automatic optimization of a pre-ventricular atrial blanking period for reliably preventing far-field R-wave sensing on the atrial channel of a dual-chamber or multi-chamber cardiac stimulation device. The algorithm presented herein may be repeated periodically such that the pre-ventricular atrial blanking period may be adjusted in response to varying conditions that increase or decrease the likelihood of far-field R-wave sensing. Stimulation device performance is improved by preventing inappropriate device responses such as mode-switching, or ventricular tracking, due to atrial detection of far-field R-waves as P-waves.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at minimizing far-field R-wave sensing on an atrial channel by providing automatic adjustment of a pre-ventricular atrial blanking period. A general cardiac stimulation device will be described in conjunction with FIGS. 1 and 2, in which the features of the present invention could be implemented. It is recognized, however, that numerous variations of such a device exist in which the methods of the present invention could be implemented without deviating from the scope of the present invention.

Figure 1:
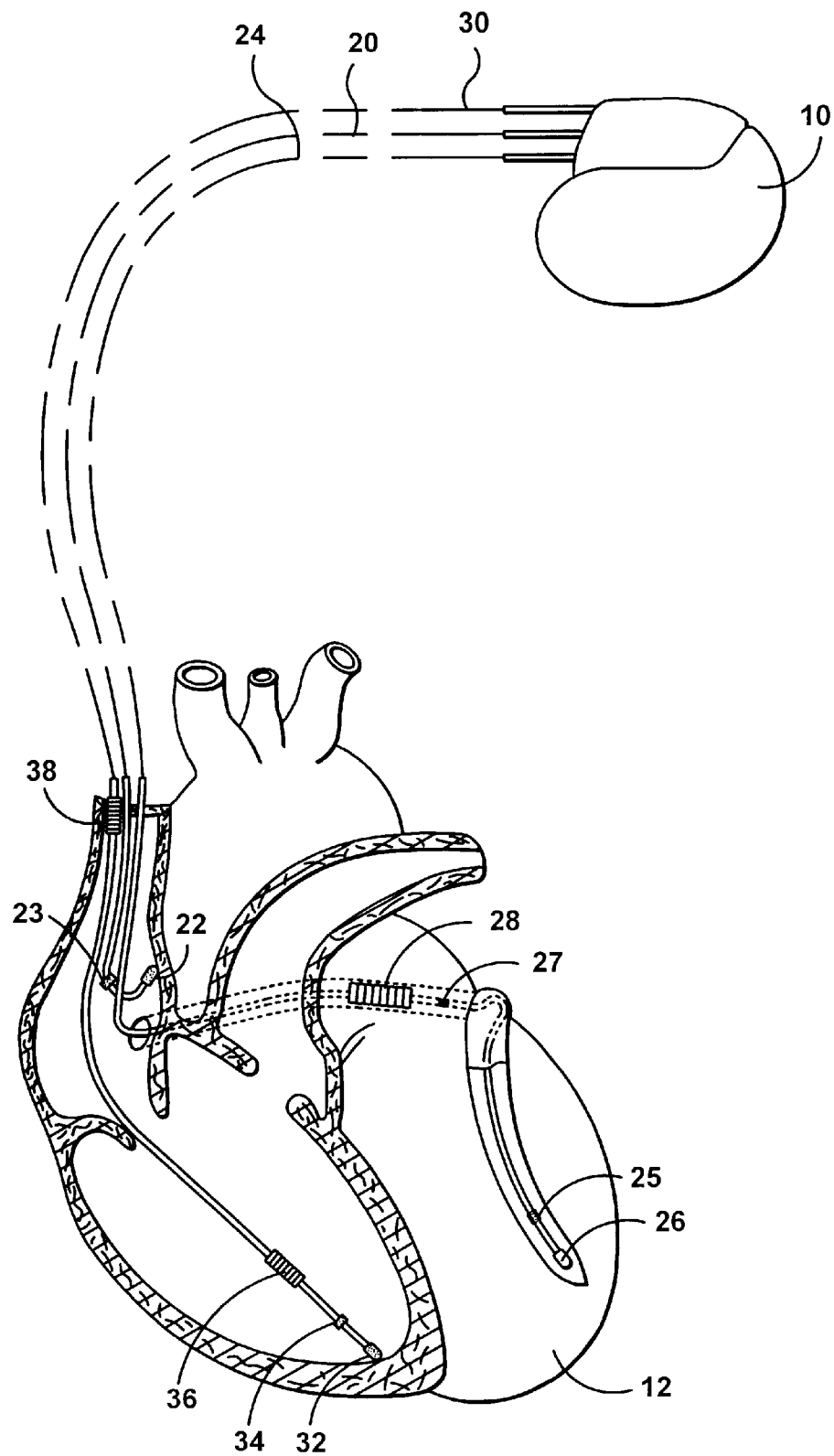
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a coronary sinus tip electrode 26 for unipolar stimulation or in combination with left ventricular ring electrode 25 for bipolar stimulation, left atrial pacing therapy using at least a coronary sinus ring electrode 27, and shocking therapy using at least a coronary sinus coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
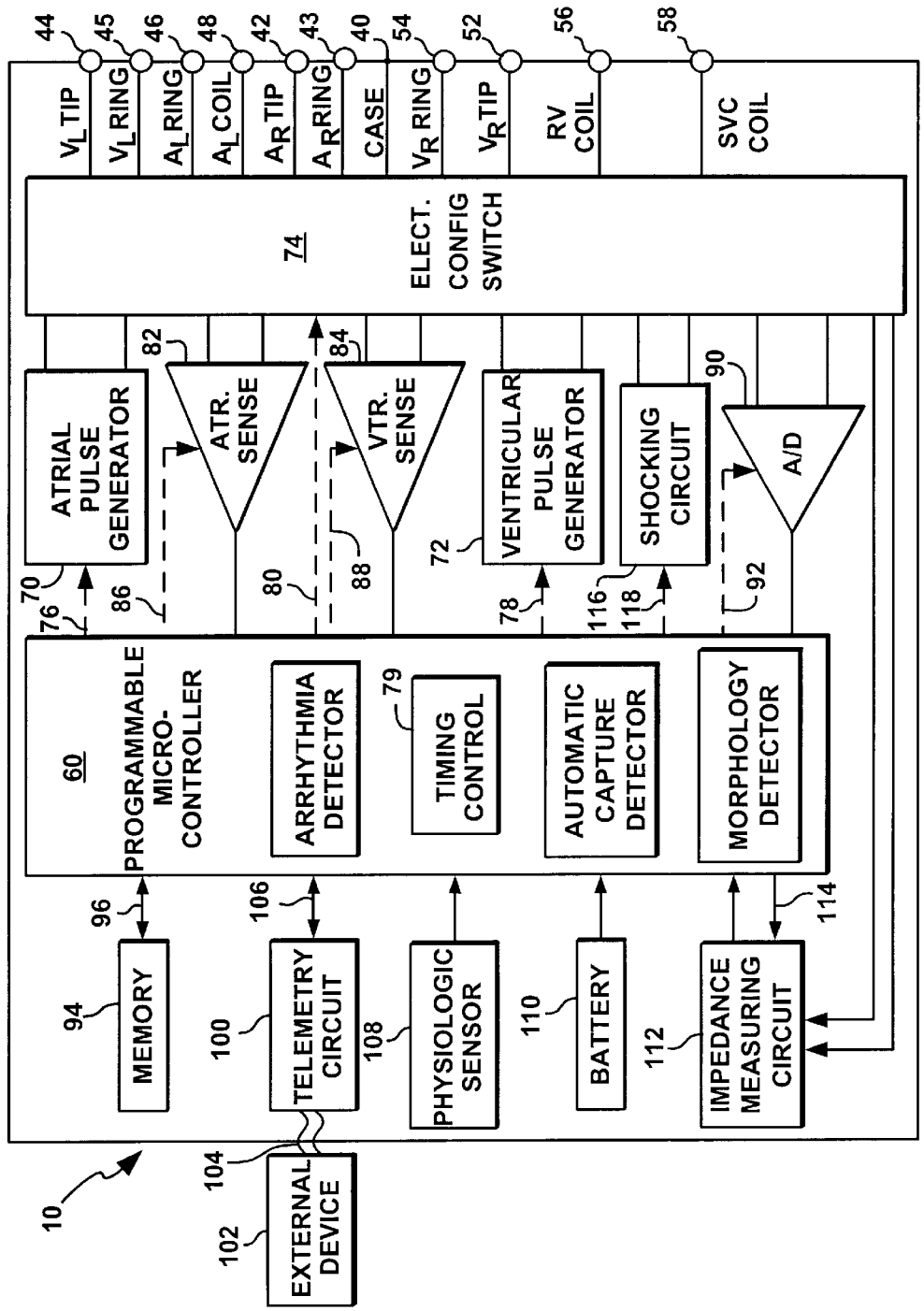
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The stimulation device 10 further includes a connector having a plurality of terminals 42, 43, 44, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23.

To achieve left chamber sensing, pacing, and shocking, the connector includes at least a left ventricular tip terminal ($V_L$ TIP) 44, a left ventricular ring terminal ($V_L$ RING), a left atrial ring terminal ($A_L$ RING) 46, and a left atrial shocking coil terminal ($A_L$ COIL) 48, which are adapted for connection to the coronary tip electrode 26, the left ventricular ring electrode 25, the coronary sinus ring electrode 27, and the coronary sinus coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, blanking intervals, noise detection windows, evoked response windows, alert intervals, marker channel timing, etc. In accordance with the present invention, the timing control circuitry 79 controls the timing of a pre-ventricular atrial blanking period determined by the methods to be presented herein.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, antitachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". When automatic capture is enabled, the microcontroller 60 searches for a depolarization signal following a stimulation pulse during a "detection window" set by timing control circuitry 79 within microcontroller 60. The microcontroller 60 enables the data acquisition system 90 via control signal 92 to sample the cardiac signal that falls in the capture detection window. The sampled signal is evaluated to determine if it is an evoked response signal based on its amplitude, peak slope, or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by means of a control signal 114.

It is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
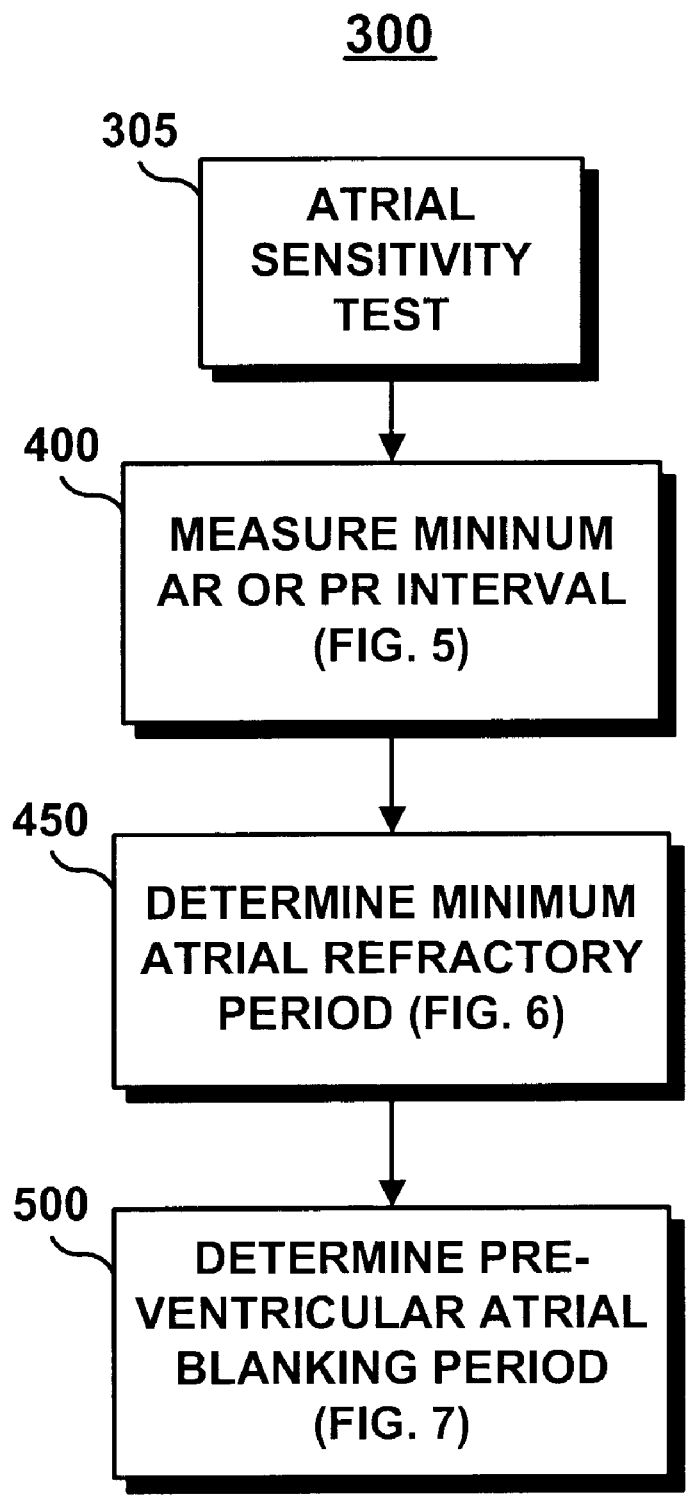
FIG. 3 is a flow chart illustrating a method of automatically determining a pre-ventricular atrial blanking period, according to the present invention.

In FIG. 3, a flow chart is shown describing an overview of the operation and novel features implemented in one embodiment of the device 10 for automatically adjusting a pre-ventricular atrial blanking period. As used herein, the pre-ventricular atrial blanking period refers to a time period preceding an intrinsic ventricular event, in which sensed intrinsic atrial events are ignored.

In the flow chart of FIG. 3, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Method 300 that is outlined in FIG. 3, should preferably not be performed in the presence of an atrial arrhythmia, and is primarily intended for use in patients exhibiting evidence of far-field R-wave sensing by the atrial channel of device 10. At step 305 of method 300, an atrial sensitivity test is performed to verify regular P-wave sensing. Prior to making any adjustments to a pre-ventricular atrial blanking period, atrial sensitivity is preferably appropriately adjusted in order to prevent inaccurate measurements of timing intervals made in subsequent steps based on sensed P-waves. The atrial sensitivity may be adjusted manually or semi-automatically during a physician office visit or by automatic atrial sensitivity tests, if available.

At step 400, the microcontroller 60 measures the shortest time interval between an atrial event and a subsequently sensed intrinsic R-wave. The atrial event may be either an atrial stimulation pulse, or an intrinsic atrial P-wave, for which these intervals are known as the minimum AR interval or PR interval, respectively. The methods for measuring the minimum AR or PR interval will be described in greater detail in conjunction with FIG. 5.

At step 450, a minimum atrial refractory period is determined. Following an atrial event, an atrial refractory period is applied by timing control circuitry 79 that generally includes both a short absolute refractory period and a longer relative refractory period. Events detected during a relative atrial refractory period are ignored for the purposes of ventricular tracking. Events occurring during the atrial refractory period are expected to be noise or non-atrial events since the atria are generally in physiologic refractory and cannot depolarize again so soon after the atrial event that triggered the refractory period.

A short atrial refractory period is desired in order to allow a maximum sensing window for detection of high atrial rates. However, too short of an atrial refractory period may allow sensing of non-atrial events. Therefore, at step 450, the minimum atrial refractory period required to prevent two consecutive atrial events within the normal range of atrial refractory period settings is determined. The method for determining a minimum atrial refractory period will be described in greater detail in conjunction with FIG. 6.

At step 500, the microcontroller 60 determines an optimal pre-ventricular atrial blanking period based on the previous determinations of a minimum AR or PR interval and a minimum atrial refractory period. The methods for optimizing a pre-ventricular atrial blanking period will be described in detail in conjunction with FIG. 7.

The operations outlined in FIG. 3 may be performed in response to a user command provided by an external programmer, or they may be preformed automatically on a periodic basis, for example once per day. When performed on a periodic basis, the frequency of adjusting the pre-ventricular atrial blanking period is preferably programmable.

Figure 4:
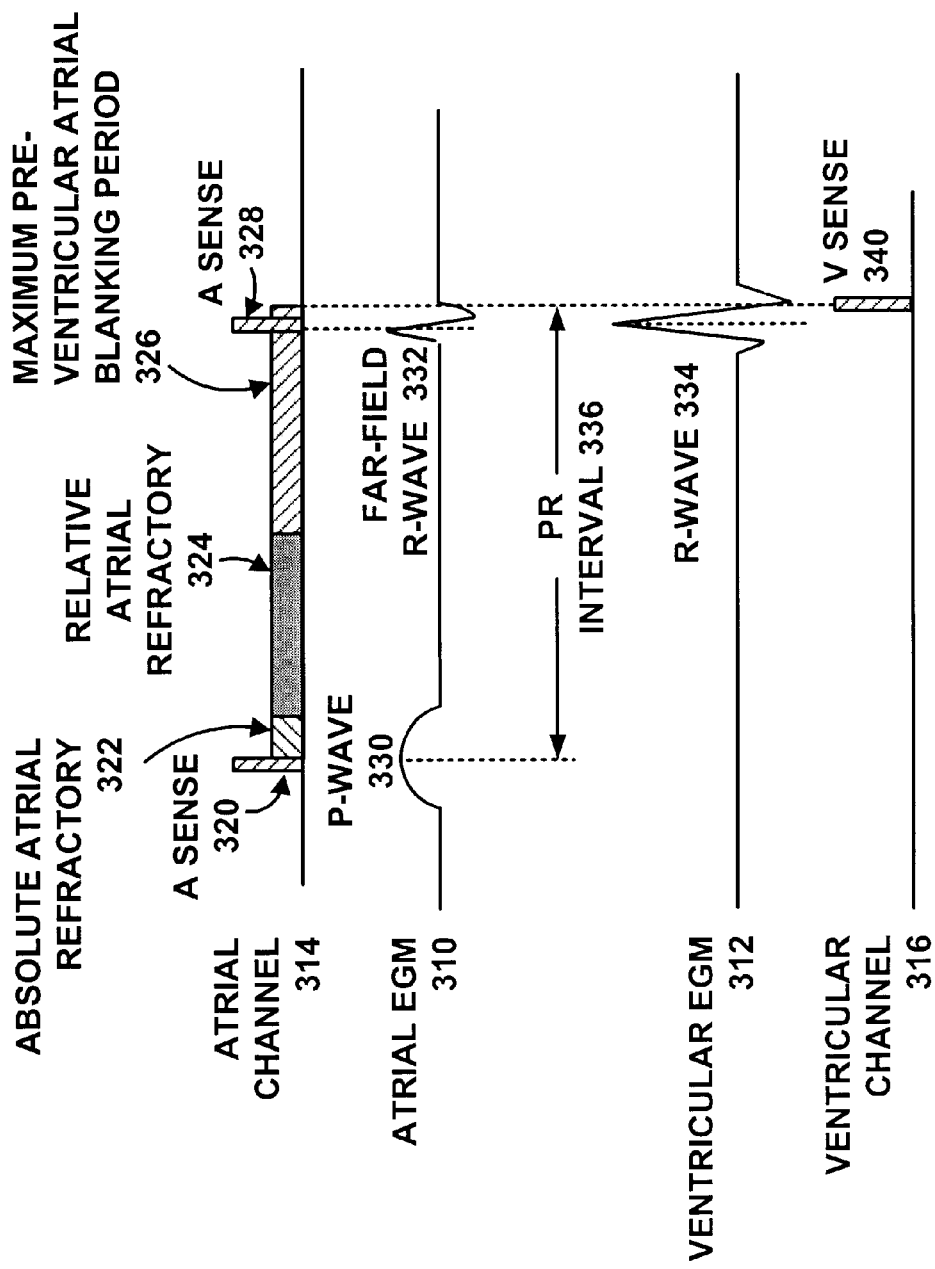
FIG. 4 is a timing diagram illustrating the relationship between atrial and ventricular events, atrial refractory periods, and a pre-ventricular atrial blanking period determined by the method of FIG. 3.

In FIG. 4, a timing diagram illustrates the relationship of the timing intervals just described, and the function of the pre-ventricular atrial blanking period in preventing atrial sensing of a far-field R-wave. An atrial EGM signal 310 is illustrated showing an intrinsic P-wave 330 and a far-field R-wave 332. A ventricular EGM signal 312 is illustrated showing an intrinsic R-wave 334 associated with the far-field R-wave 332 visible on the atrial EGM 310.

Atrial sensed events and timing intervals corresponding to the atrial EGM 310 signals are depicted on the atrial channel 314. An atrial sensed event (A SENSE) 320 corresponds with the P-wave 330. This atrial sensed event 320 triggers an atrial refractory period comprised of an absolute atrial refractory period 322, typically on the order of 16 ms, and a longer relative atrial refractory period 324, typically on the order of 50 to 100 ms.

The ventricular sensed event (V SENSE) 340 corresponding to the intrinsic R-wave 334 is depicted on the ventricular channel 316. The interval between the atrial sense (A SENSE) 320 of the intrinsic P-wave 330 and the ventricular sense (V SENSE) 340 of the intrinsic R-wave is the PR interval 336. The difference between the PR interval 336 and the atrial refractory period, including the absolute atrial refractory 322 and the relative atrial refractory 324, represents the maximum pre-ventricular atrial blanking period 326.

The illustration of FIG. 4 shows that the ventricular sense 340 can lag slightly behind the actual R-wave signal 334 and far-field R-wave signal 332. This lag may be present due to ventricular gain and sensitivity settings and functioning of the device (10) electronics. Thus, it is possible for the atrial channel 314 to sense a far-field R-wave 332 prior to the ventricular channel 316 sensing the R-wave 334.

This situation is depicted in FIG. 4 where an atrial sense (A SENSE) 328 associated with the far-field R-wave 332 occurs on the atrial channel 314 prior to the ventricular sense 340 associated with the R-wave 334. However, the maximum pre-ventricular blanking period 326 can be seen to extend beyond the atrial sense 328 of the far-field R-wave signal 332 to the time corresponding with the actual ventricular sense 340 of the R-wave signal 334. This pre-ventricular atrial blanking period is a relative blanking period applied within the logic of microprocessor 60, such that microcontroller 60 will not recognize the atrial sense 328 as a true atrial event when it occurs within the pre-ventricular atrial blanking period 326.

Figure 5:
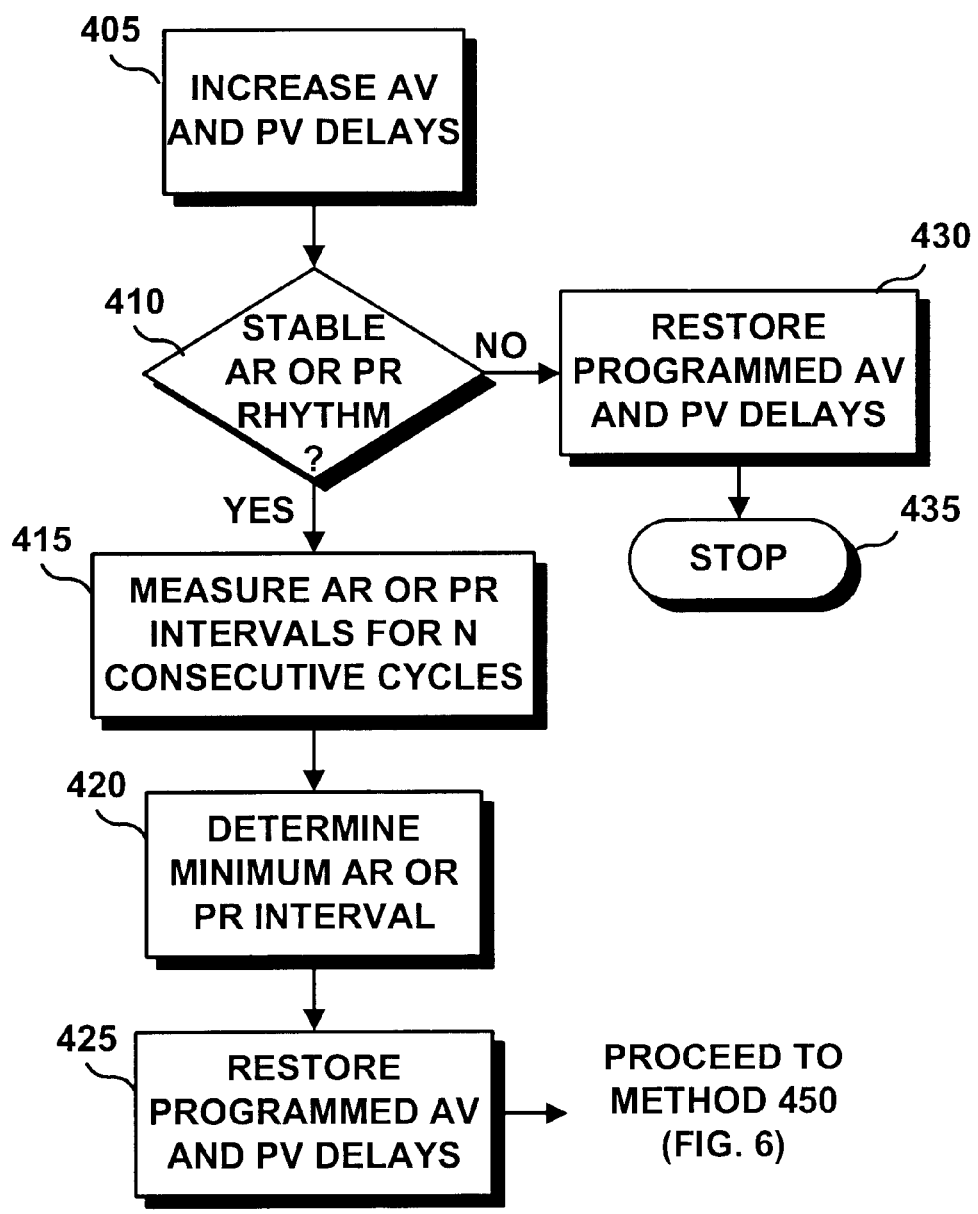
FIG. 5 is a flow chart illustrating a method of determining a minimum AR or PR interval.

The details of the steps performed in one embodiment of the present invention for determining a minimum PR or AR interval are shown in FIG. 5. At step 405, the programmed AV and PV delay settings are automatically increased. This adjustment is made to allow more time for an intrinsic R-wave to occur following each atrial event. Therefore, at step 410, the microprocessor 60 verifies that the operating mode of device 10 is a stable AR (atrial stimulation followed by ventricular sensed R-wave) or PR (atrial sensed P-wave followed by ventricular sensed R-wave) rhythm. If stable ventricular R-wave sensing is not established, the programmed AV and PV delay settings are restored at step 430 and the algorithm 400 is terminated at step 435. If ventricular stimulation continues rather than ventricular sensing, intrinsic R-waves do not occur therefore setting a pre-ventricular atrial blanking period is unnecessary.

If stable ventricular sensing is established, the AR or PR intervals are measured for a predetermined number of cardiac cycles, for example 10 cycles, at step 415. At step 420, the minimum AR or PR interval is determined and this value will be temporarily stored in memory 94. At step 425, the programmed AV and PV delays are restored and the algorithm 400 proceeds to step 450 (FIG. 3) for determining the minimum atrial refractory period.

Figure 6:
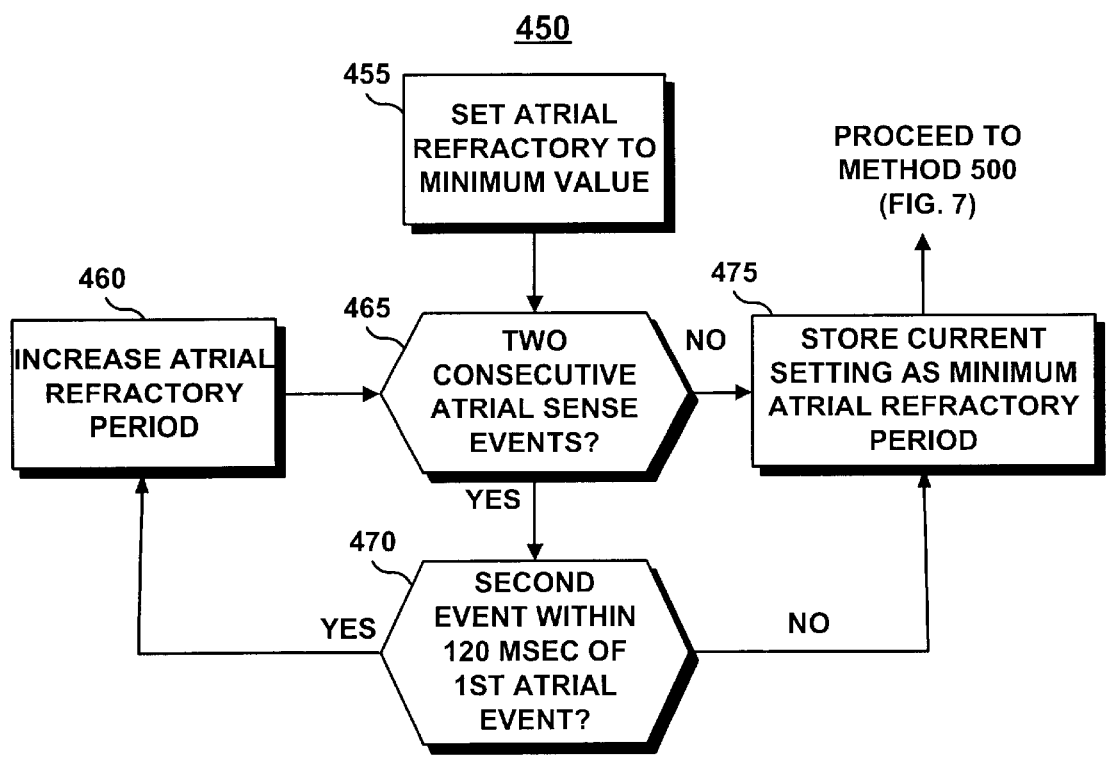
FIG. 6 is a flow chart illustrating a method of automatically determining a minimum atrial refractory period.

The steps performed in one embodiment of the present invention for determining the minimum atrial refractory period are shown in FIG. 6. At step 455, the atrial refractory period is set to the shortest available setting. Typically the atrial refractory period includes a fixed absolute refractory period, on the order of 16 ms, and a programmable relative atrial refractory period, normally ranging between 50 and 120 ms. Therefore at step 455, the relative atrial refractory period would be set to the minimum available setting, for example 50 ms. At step 465, microprocessor 60 determines if two consecutive atrial events occur at the shortened atrial refractory period. The first event may be either a stimulated or sensed event and the second event will be an atrial sensed event. If this occurs, and the second event is within 120 ms of the first event as determined at decision step 470, then the atrial refractory period is too short. The atrial refractory period is thus lengthened, preferably by one programmable step, at step 460.

If a second atrial event occurs later than 120 ms after the first atrial event, it is presumed to be either a real atrial event, or a far-field R-wave. Therefore, once the conditions are met at decision step 465 and 470, that is two consecutive atrial events do not occur within a 120 ms interval, then the atrial refractory period is stored as the minimum atrial refractory period at step 475. The algorithm 450 then proceeds to step 500 (FIG. 3), to proceed with adjusting the pre-ventricular atrial blanking period.

Figure 7:
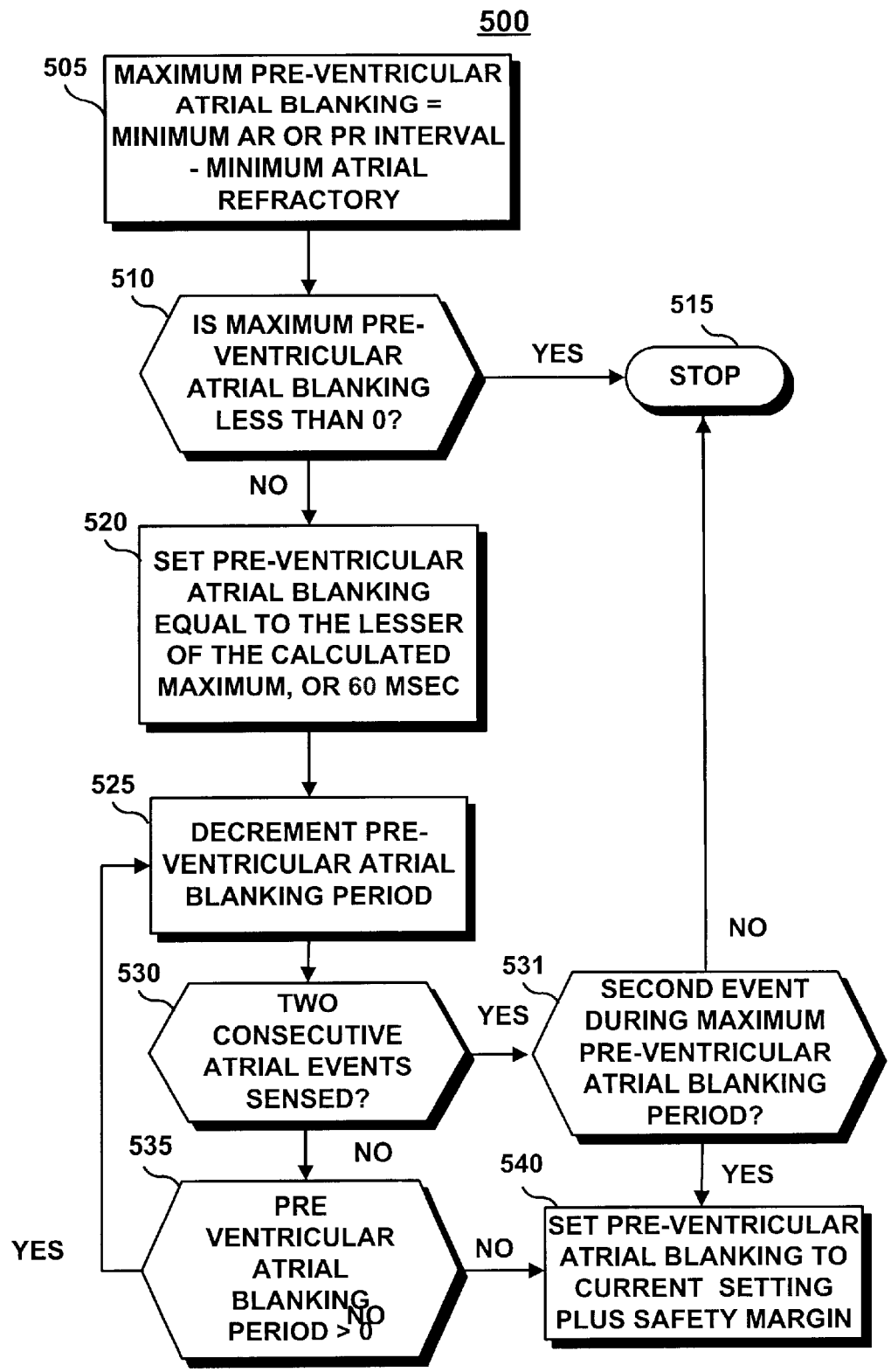
FIG. 7 is a flow chart illustrating a method of automatically adjusting a pre-ventricular atrial blanking period.

In FIG. 7, the methods included in one embodiment of the present invention to be performed at step 500 of FIG. 3 are outlined in greater detail. Beginning at step 505, the maximum pre-ventricular atrial blanking period is calculated as the difference between the minimum PR interval and the minimum atrial refractory period.

At step 510, the maximum pre-ventricular atrial blanking period is verified to be greater than zero. If not, the algorithm 500 is terminated at step 515. In this situation, the atrial refractory period extends beyond the minimum AR or PR interval thus the pre-ventricular atrial blanking period is not required to prevent far-field R-wave sensing.

If a positive value for the maximum pre-ventricular atrial blanking period is found at decision step 510, then the pre-ventricular atrial blanking period is set to either a predetermined maximum setting (e.g., 60 ms), to the maximum pre-ventricular atrial blanking period calculated at step 505, or to the lesser of the predetermined maximum setting or the calculated maximum pre-ventricular atrial blanking period. At step 525, the pre-ventricular atrial blanking period is shortened, preferably by a predetermined interval.

At step 530, microprocessor 60 determines if two consecutive atrial events are sensed prior to a ventricular event. The first atrial event may be either an atrial stimulation or an atrial sense. The second event may either be a far-field R-wave artifact, or an atrial sense event since it is sensed past the adjusted atrial refractory.

At step 531, if the second atrial event is sensed during the maximum pre-ventricular atrial blanking period, it is presumed to be a far-field R-wave because the pre-ventricular atrial blanking interval has become too short to effectively prevent far-field R-wave sensing. If the second atrial event is sensed prior to the maximum pre-ventricular atrial blanking period, the algorithm 500 is terminated at step 515. In this situation the atrial rhythm is considered unstable.

If two consecutive atrial events do not occur at decision step 530, the pre-ventricular atrial blanking interval continues to be decreased up to a minimum value of zero as determined at decision step 535. Once two consecutive atrial events do occur as determined at decision step 530, the pre-ventricular atrial blanking interval has become too short to effectively prevent far-field R-wave sensing.

Thus, at step 540, the pre-ventricular atrial blanking period is set at the current setting plus a safety margin so that blanking period will extend beyond the far-field R-wave signal. The safety margin may be fixed or programmable value and will typically be on the order of between about 10 and about 20 ms, for example about 16 ms. The safety margin should not cause the pre-ventricular atrial blanking period to exceed the calculated maximum atrial blanking period, and in that case, the pre-ventricular atrial blanking period would be set to the maximum calculated value.

While the methods outlined in FIG. 7 indicate that the pre-ventricular atrial blanking period is progressively decreased until two consecutive atrial events occur, numerous search algorithms are available, such as binary search algorithms, which may be used to determine the setting at which two atrial events first occur in an efficient manner.

Figure 8:
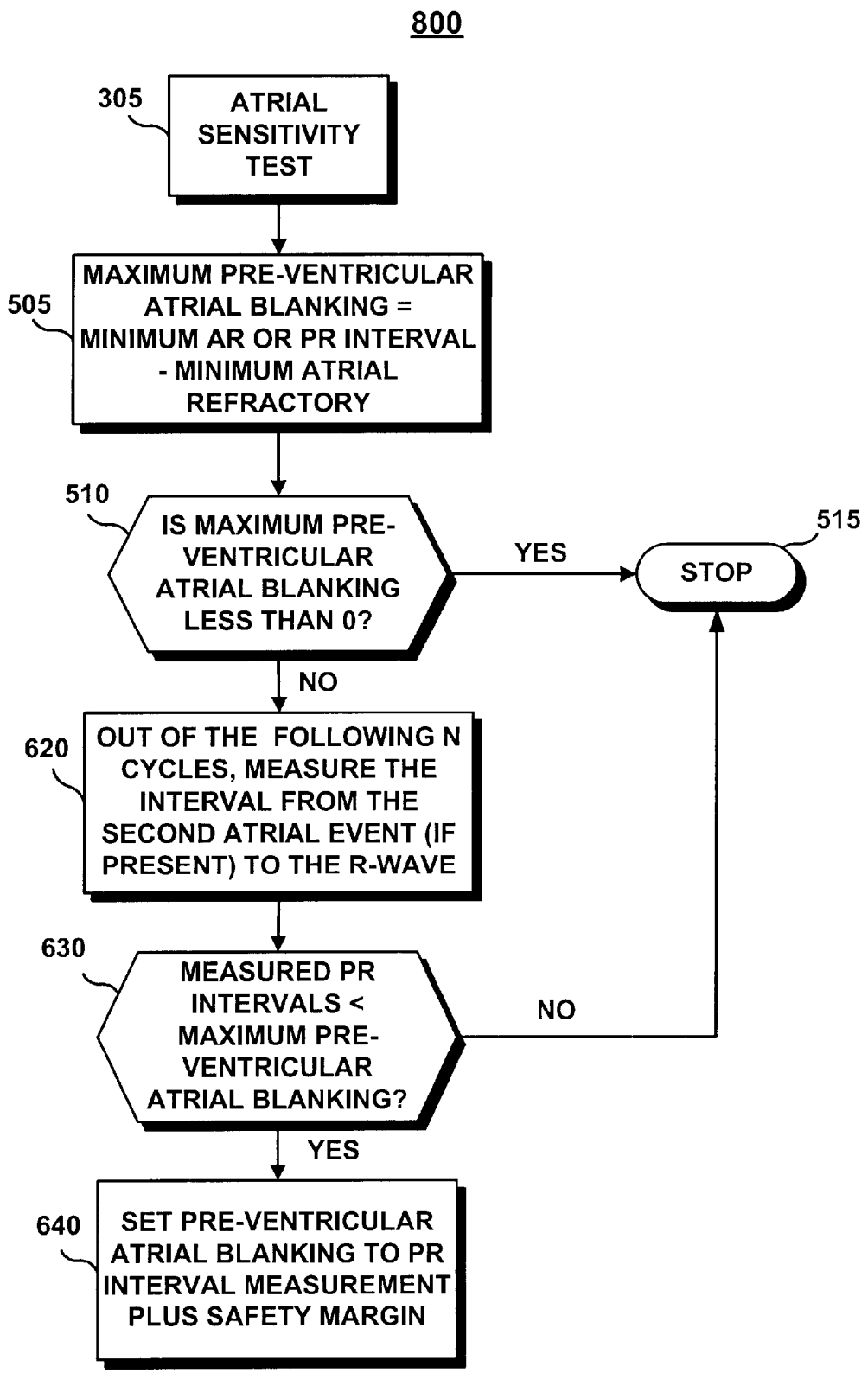
FIG. 8 is a flow chart illustrating an alternative method of the present invention for automatically adjusting a pre-ventricular atrial blanking period.

In FIG. 8, a flow chart is shown depicting an alternative method 800 of the present invention for automatically adjusting a pre-ventricular atrial blanking period. In this embodiment, the atrial sensitivity is first adjusted at step 305 to ensure accurate P-wave sensing. At step 505, and 510 the maximum pre-ventricular atrial blanking period is calculated according to the method described earlier in conjunction with FIG. 7.

At step 620, microprocessor 60 detects if two consecutive atrial events occur prior to an intrinsic R-wave, and measures the PR intervals from the second atrial event to the following R-wave. This step 620 is repeated for a predetermined number "N" of cycles.

At step 630, if method 800 determines that two consecutive atrial events have occurred, the microprocessor 60, then determines if the second atrial event has occurred within the maximum pre-ventricular atrial refractory period calculated at step 510. If the second atrial event did occur in that period of time, it is likely to be a far-field R-wave that slightly precedes the R-wave sensed on the ventricular channel. If, however, the second atrial event occurred prior to this period, but after the adjusted atrial refractory period, the atrial rhythm is considered unstable. In this case, method 800 is terminated at step 515.

At step 640, the pre-ventricular atrial blanking period is set equal to measurement made at step, 620 plus a safety margin as described previously in conjunction with FIG. 7.

Thus, a system and method have been described for automatically adjusting a pre-ventricular atrial blanking period. By providing an optimized pre-ventricular atrial blanking period, errant sensing of far-field R-waves by the atrial channel is reduced such that inappropriate stimulation device responses to sensed far-field R-waves, such as mode switching or ventricular tracking, are prevented. While detailed descriptions of specific embodiments of the present invention have been provided, it would be apparent to those reasonably skilled in the art that numerous variations of the methods described herein are possible in which the concepts of the present invention may readily be applied. The descriptions provided herein, therefore, are for the sake of illustration and are not intended to be exclusive.

What is claimed is:

1. A method of automatically adjusting a pre-ventricular atrial blanking period for use with a cardiac stimulation device, the method comprising:
   measuring an atrial-ventricular interval as a time interval between an atrial event and an intrinsic ventricular event;
   measuring a minimum atrial refractory value;
   determining a maximum pre-ventricular atrial blanking period based on the measured atrial-ventricular interval and atrial refractory value; and
   decrementing the pre-ventricular atrial blanking period from the maximum pre-ventricular atrial blanking period to a particular value that results in a second of two consecutive atrial events occurring during the pre-ventricular atrial blanking period; and
   setting the pre-ventricular atrial blanking period to a value based on the particular value.

2. The method of claim 1, further comprising setting the pre-ventricular atrial blanking period as an interval that precedes the intrinsic ventricular event and that extends to a time at which a far-field R-wave is expected to occur.

3. The method of claim 2, wherein measuring the atrial-ventricular interval comprises measuring an interval between a sensed intrinsic atrial event and the intrinsic ventricular event.

4. The method of claim 2, wherein measuring the atrial-ventricular interval comprises measuring an interval between a paced event and the intrinsic ventricular event.

5. The method of claim 4, wherein measuring the atrial-ventricular interval comprises measuring a minimum atrial-ventricular interval.

6. The method of claim 5, further comprising adjusting an atrial sensitivity.

7. The method of claim 6, further comprising verifying a stable atrial rhythm.

8. The method of claim 7, wherein measuring the atrial-ventricular interval comprises measuring atrial-ventricular intervals for a predetermined number of cardiac cycles.

9. The method of claim 2, wherein determining the maximum pre-ventricular atrial blanking period comprises determining a minimum atrial refractory period by:
   setting a minimum available atrial refractory period; and
   increasing the minimum atrial refractory period until two consecutive atrial events do not occur within a predetermined time interval.

10. The method of claim 9, wherein determining the maximum pre-ventricular atrial blanking period comprises calculating a difference between the minimum atrial refractory period and the minimum atrial-ventricular interval.

11. A method of automatically adjusting a pre-ventricular atrial blanking period for use with a cardiac stimulation device, the method comprising:
   setting an initial pre-ventricular atrial blanking period to a preliminary value, wherein the preliminary value is related to at least one of a predetermined value, a maximum pre-ventricular atrial blanking period, a minimum atrial-ventricular interval, and a minimum atrial refractory value;
   monitoring for at least two consecutive atrial events without an intervening ventricular event using the preliminary value, where the second of the two consecutive atrial events occurs during the pre-ventricular atrial blanking period;
   decrementing the preliminary value if said events are not detected; and
   setting the pre-ventricular atrial blanking period based on the current preliminary value if said events are detected.

12. The method of claim 11, wherein setting the pre-ventricular atrial blanking period comprises setting the pre-ventricular atrial blanking period to the preliminary value plus a safety margin.

13. The method of claim 12, wherein decrementing comprises gradually decrementing the pre-ventricular atrial blanking interval.

14. The method of claim 13, wherein gradually decrementing the pre-ventricular atrial blanking period comprises setting the pre-ventricular atrial blanking period to a shortest interval at which two consecutive atrial events do not occur.

15. The method of claim 14, wherein setting the pre-ventricular atrial blanking period comprises setting the pre-ventricular atrial blanking period equal to the longest setting at which two consecutive atrial events occur plus a predetermined safety margin.

16. The method of claim 11, further comprising automatically adjusting the pre-ventricular atrial blanking period on a periodic basis.

17. The method of claim 11, further comprising determining if the first and second consecutive atrial events occur prior to a ventricular event; and
   measuring the atrial-ventricular interval from the second atrial event to the ventricular event.

18. A cardiac stimulation device that automatically adjusts a pre-ventricular atrial blanking period, the device comprising:

a pulse generator that selectively generates stimulation energy;

a detector that monitors for atrial events; and circuitry that sets a pre-ventricular atrial blanking period to a preliminary value, and wherein the circuitry is responsive to signals from the detector (1) to monitor for at least two consecutive atrial events without an intervening ventricular event using the preliminary value, where the second of the two consecutive atrial events occurs during the pre-ventricular atrial blanking period, (2) to decrement the preliminary value if said events are not detected, and (3) to set the pre-ventricular atrial blanking period to a value based on the current preliminary value if said events are detected.

19. The device of claim 18, wherein the pre-ventricular atrial blanking period comprises an interval that precedes the intrinsic ventricular event and that extends to a time at which a far-field R-wave is expected to occur.

20. The device of claim 18, wherein an atrial-ventricular interval comprises an interval between a sensed intrinsic atrial event and the intrinsic ventricular event.

21. The device of claim 18, wherein an atrial-ventricular interval comprises an interval between a stimulation atrial event and the intrinsic ventricular event.

22. The device of claim 21, wherein the atrial-ventricular interval comprises a minimum atrial-ventricular interval.

23. The device of claim 22, wherein the circuitry determines a minimum artial refactory period by:

setting a minimum available atrial refractory period; and increasing the minimum atrial refractory period until two consecutive atrial events do not occur within a predetermined time interval.

24. The device of claim 23, wherein the circuitry determines a maximum pre-ventricular artial blanking period by calculating a difference between the minimum atrial refractory period and the minimum atrial-ventricular interval.

25. The device of claim 18, wherein the timing control circuit decrements the pre-ventricular atrial blanking period to the optimal value by setting the pre-ventricular atrial blanking period to a shortest interval at which two consecutive atrial events do not occur.

26. The device of claim 18, further comprising a controller that measures an atrial-ventricular interval as a time interval between an atrial event and an intrinsic ventricular event.

27. A cardiac stimulation device that automatically adjusts a pre-ventricular atrial blanking period, comprising:

means for setting a pre-ventricular atrial blanking period to a preliminary value;

means for adjusting the preliminary value to a final value at which a second of two consecutive atrial events occurs during the blanking period; and means for setting the blanking period to a value that is related to the final value.

28. The device of claim 27, wherein the pre-ventricular atrial blanking period comprises an interval that precedes the intrinsic ventricular event and that extends to a time at which a far-field R-wave is expected to occur.

29. The device of claim 27, wherein the atrial-ventricular interval comprises an interval between a sensed intrinsic atrial event and the intrinsic ventricular event.

30. The device of claim 27, wherein the atrial-ventricular interval comprises an interval between a stimulation atrial event and the intrinsic ventricular event.

31. The device of claim 27, wherein the means for setting comprises means for setting the blanking period to the final value plus a safety margin.

32. The device of claim 27, wherein the means for adjusting comprises means for decrementing the preliminary value by a predetermined amount.

* * * * *